United States Patent
Cucin (12) United States Patent (10) Patent No.: US 8,348,929 B2
Cucin (45) Date of Patent: Jan. 8, 2013

(54) ENDOSCOPICALLY-GUIDED TISSUE ASPIRATION SYSTEM FOR SAFELY REMOVING FAT TISSUE FROM A PATIENT

(75) Inventor: Robert L. Cucin, West Palm Beach, FL (US)

(73) Assignee: Rocin Laboratories, Inc., West Palm Beach, FL (US)

( * ) Notice: Subject to any disclaimer, the term of this patent is extended or adjusted under 35 U.S.C. 154(b) by 442 days.

(21) Appl. No.: 12/462,596

(22) Filed: Aug. 5, 2009

(65) Prior Publication Data

US 2011/0034905 A1 Feb. 10, 2011

(51) Int. Cl.
*A61B 18/14* (2006.01)
(52) U.S. Cl. ...................................... 604/542
(58) Field of Classification Search .................. 604/319, 604/540–544; 606/32, 40; 600/109, 110, 600/204, 425
See application file for complete search history.

(56) References Cited

U.S. PATENT DOCUMENTS

| | | | |
|---|---|---|---|
| 4,030,162 A | 6/1977 | Hubbard | |
| 4,617,013 A | 10/1986 | Betz | |
| 5,112,302 A | 5/1992 | Cucin | |
| 5,154,664 A | 10/1992 | Hazenbroek et al. | |
| 5,226,429 A | 7/1993 | Kuzmak | |
| 5,254,117 A | 10/1993 | Rigby et al. | |
| 5,300,069 A | 4/1994 | Hunsberger et al. | |
| 5,329,943 A | 7/1994 | Johnson | |
| 5,348,535 A | 9/1994 | Cucin | |
| 5,372,945 A | 12/1994 | Alchas et al. | |
| 5,380,277 A | 1/1995 | Phillips | |
| 5,514,084 A | 5/1996 | Fisher | |
| 5,643,198 A | 7/1997 | Cucin | |

(Continued)

FOREIGN PATENT DOCUMENTS

WO 2011/017517 A1 2/2011

OTHER PUBLICATIONS

International Search Report, International Application No. PCT/US 10/44543, Jan. 6, 2011.

(Continued)

*Primary Examiner* — Melanie Hand
(74) *Attorney, Agent, or Firm* — Thomas J. Perkowski, Esq., P.C.

(57) ABSTRACT

An endoscopically-guided power-assisted tissue aspiration method of and system for safely removing fat tissue from the mesenteric region of a patient. The endoscopically-guided power-assisted tissue aspiration system includes: an endoscopy system having a video probe, one or more video monitors, and digital recording equipment; and a power-assisted tissue aspiration system including a powered hand-supportable instrument including a hand-supportable housing and being provided with a twin-cannula assembly including an inner cannula mounted for reciprocating movement within an outer cannula; a source of power operably connected to the powered hand-supportable instrument, for supplying power to drive the inner cannula to reciprocate said inner cannula within the outer cannula during tissue aspiration operations; and a vacuum pump operably connected to the inner cannula, for aspirating visceral fat tissue from the mesenteric region of the patient, through outer and inner aspiration apertures of the twin-cannula assembly, while the video probe is capturing digital images of fat tissue within the FOV, the video monitor is displaying the captured digital images of fat tissue being removed from the mesenteric region of the patient, and the digital recording equipment is recording the same.

11 Claims, 8 Drawing Sheets

U.S. PATENT DOCUMENTS

| | | | |
|---|---|---|---|
| 5,655,544 | A | 8/1997 | Johnson |
| 5,665,100 | A | 9/1997 | Yoon |
| 5,720,762 | A | 2/1998 | Bass |
| 5,746,762 | A | 5/1998 | Bass |
| 5,769,879 | A | 6/1998 | Richards et al. |
| 5,795,323 | A | 8/1998 | Cucin |
| 6,149,610 | A | 11/2000 | Urko |
| 6,208,903 | B1 | 3/2001 | Richards et al. |
| 6,302,863 | B1 | 10/2001 | Tankovich |
| 6,315,756 | B1 | 11/2001 | Tankovich |
| 6,316,247 | B1 | 11/2001 | Katz et al. |
| 6,346,107 | B1 | 2/2002 | Cucin |
| 6,371,911 | B1 | 4/2002 | Hossain et al. |
| 6,394,973 | B1 | 5/2002 | Cucin |
| 6,514,215 | B1 | 2/2003 | Ouchi |
| 6,544,211 | B1 | 4/2003 | Andrew et al. |
| 6,605,080 | B1 | 8/2003 | Altshuler et al. |
| 6,626,890 | B2 * | 9/2003 | Nguyen et al. ............... 604/542 |
| 6,652,522 | B2 | 11/2003 | Cucin |
| 6,676,629 | B2 | 1/2004 | Andrew et al. |
| 6,697,670 | B2 | 2/2004 | Chomenky et al. |
| 6,761,701 | B2 | 7/2004 | Cucin |
| 6,795,728 | B2 | 9/2004 | Chornenky et al. |
| 6,872,199 | B2 | 3/2005 | Cucin |
| 6,892,099 | B2 | 5/2005 | Jaafar et al. |
| 6,902,559 | B2 | 6/2005 | Taufig |
| 6,916,328 | B2 | 7/2005 | Brett |
| 7,037,344 | B2 | 5/2006 | Kagan et al. |
| 7,048,683 | B2 | 5/2006 | Borst et al. |
| 7,060,061 | B2 | 6/2006 | Altshuler et al. |
| 7,060,079 | B2 | 6/2006 | Wulc et al. |
| 7,112,200 | B2 | 9/2006 | Cucin |
| 7,381,206 | B2 | 6/2008 | Cucin |
| 7,384,417 | B2 | 6/2008 | Cucin |
| 7,740,605 | B2 | 6/2010 | Cucin |
| 7,775,973 | B2 | 8/2010 | Okada et al. |
| 7,779,845 | B2 | 8/2010 | Ortiz |
| 7,780,684 | B2 | 8/2010 | Wule et al. |
| 7,896,890 | B2 | 3/2011 | Ortiz et al. |
| 7,901,672 | B2 | 3/2011 | Fraser et al. |
| 8,119,121 | B2 | 2/2012 | Fraser et al. |
| 8,152,821 | B2 | 4/2012 | Gambale et al. |
| 2002/0151874 | A1 | 10/2002 | Kolster et al. |
| 2006/0247514 | A1 | 11/2006 | Panasyuk et al. |
| 2007/0005082 | A1 | 1/2007 | Kraemer et al. |
| 2007/0055292 | A1 | 3/2007 | Ortiz et al. |
| 2007/0129735 | A1 | 6/2007 | Filipi et al. |
| 2007/0167963 | A1 | 7/2007 | Deem et al. |
| 2007/0175488 | A1 | 8/2007 | Cox et al. |
| 2007/0239176 | A1 | 10/2007 | Stokes et al. |
| 2009/0192498 | A1 * | 7/2009 | Andrew et al. ............... 604/542 |

OTHER PUBLICATIONS

Amelioration of diet-induced diabetes mellitus by removal of visceral fat by Cid Pitombo, Eliana P. Araujo, Claudio T. De Souza, Jose C. Pareja, Bruno Geloneze and Licio A. Velloso. Journal of Endocrinology (2006) 191, 699-706, Society for Endocrinology, printed in Great Britain, 8 pages.

Guidelines on Laparoscopy, European Association of Urology, J.D. Doublet, G. Janetshek, A. Joyce, A. Mandressi, J. Rassweiller, D. Tolley, 2002, 38 pages.

Adipose Tissue as an Endocrine Organ, by Erin E. Kershaw and Jeffrey S. Flier; Division of Endocrinology, Dept. of Medicine Beth Israel Deaconess Medical Center, Boston MA 02215; Journal of Clinical Endocrinology & Metabolism 89(6): pp. 2548-2556, Copyright 2004 by the Endocrine Society. 9 pages.

Large-Volume Liposuction and Extensive Abdominoplasty: a feasible alternative for improving body shape by Carenas-Camarena, Lazaro M.D.; Gonzalez, Luis M.D.; Plastic & Reconstructive Surgery: Oct. 1998—vol. 102—Issue 5—pp. 168-1707. 9 pages.

Surgical removal of visceral adipose tissue: effects on insulin action. Gabriely I, Barzaila N.; Institute for Aging Research, Belfer Bldg. #701, Albert Einstein College of Medicine, 1300 Morris Park Avenue, Bronx NY 10461 USA. 6 pages.

Adipokines: the missing link between insulin resistance and obesity by Antuna-Puente B., Feve B., Fellahi S., Bastard J.P.; Inserm U680, faculte de medecine Saint-Antoine, university Pierre-et Marie Curie, Paris 6, 75012, Paris, France; Diabetes Metab. Feb. 2008; 34(1): 2-11. 10 page.

The role of TNF-alpha in insulin resistance. Borst SE. Dept. of Exercise & Sport Sciences, University of Florida, Malcom Randall VA Medical Center, Gainesville FL 32608-1197, USA seborst@ufi.edu; Endocrine Mar.-Apr. 2004; 23(2-3) 177-82. 6 pages.

Diabetes: insulin resistance and derangements in lipid metabolism. Cure through intervention in fat transport and storage. Raz I., Eldor R., Cernea S., Shafrir E.; Dept. of Medicine, Diabetes Ctr., Hadassah University Hospital, Jerusalem 91120, Israel. ntv502@netvision.net.il. Diabetes Metab Res Rev. Jan.-Feb. 2005; 21(1) 3-14. 12 pages.

Novel Interactions of Adiponectin with the Endocrine System and Inflammatory Parameters by Jose Manuel Fernandez-Real, Abel Lopez-Bermejo, Roser Casamitjana and Wifredo Ricart; Unit of Diabetes, Endocrinology and Nutrition, Dept. of Internal Medicine, University Hospital of Girona "Dr. Josep Trueta," 17007 Girona, Spain; The Journal of Clinical Endocrinology & Metabolism 88(6): 2714-2718; Copyright 2003 by The Endocrine Society doi: 10.1210/jc.2002-021583. 5 pages.

Obesity in the new millennium (Abstract). Friedman JM. The Rockefeller University, New York NY 10021-6399 USA; Nature 2000 Apr. 6, 404 (6778) 632-4. 1 page.

Leptin and the Regulation of Body Weight by Jeffrey M. Friedman, Rockefeller University, New York NY 10065 USA fried@mail.rockefeller.edu; Copyright 2011 by the Keo Journal of Medicine. 9 pages.

Improvements in cardiovascular risk profile after large-volume lipoplasty: a 1-year follow-up study by Giese SY, Neborsky R, Bulan EJ, Spear SL, Yanovski, JA; Aesthet Surg J Nov. 2001 21(6): 527-31. 5 pages.

Effect of Liposuction on insulin resistance and vascular inflammatory markers in obese women by G. Giugliano, G. Nicolletti, E. Grelia, F. Giugliano, K. Esposito, N. Scuderi, F. D'Andrea; British Journal of Plastic Surgery, of. vol. 57, Issue 3, pp. 190-194, Apr. 2004. 5 pagess.

The effects of surgically removing subcutaneous fat on the metabolic profile and insulin sensitivity in obese women after large-volume liposuction treatment (Abstract). Gonzalez-Ortiz M., Robles-Cervantes JA, Cardenas-Camarena L., Bustos-Saldana R., Martinez-Abundis E.; Medial Research Unit in Clinical Epidemiology, West National Medical Center, Mexican Institute of Social Security, Guadalajara, Mexico. uiec@Prodigy.net.mx. Horn Metab Res. Aug. 2002; 34(8): 446-9. 1 page.

Modification of insulin, glucose and cholesterol levels in nonobese women undergoing liposuction, is liposuction metabolically safe? Robles-Cervantes JA, Yanez-Diaz S., Cardenas-Camarena L.; Ann Plast Surg. Jan. 2004; 52(1): 64-7. 4 pages.

Mechanism of the Postreceptor Defect in Insulin Action in Human Obesity: Decrease in Glucose Transport System Activity; Theodore P. Ciaraldi, Orville G. Kolterman, and Jerrold M. Olefsky, Dept. of Medicine, University of Colorado Health Sciences Ctr., Div. of Endocrinology/Metabolism, Denver CO 80262; J. Clin. Invest. The American Soc. or Clinical Investigation, Inc., 0021-9738/81/10/0875/06, vol. 68, Oct. 1981, pp. 875-880. 6 pages.

Historical perspective: visceral obesity and related comorbidity in Joannes Bapista Morgagni's 'De sedibus et causis morborum per anatomen indagata' by Enzi G. Busetto L., Inelmen EM, Coin A., Sergi G.; Dept. of Medical and Surgical Sciences, Univ. of Padova, Italy. Int J Obes Relat Metab Disord. Apr. 2003; 27(4):534-5. 2 pages.

Omentectomy and Metabolic Syndrome. ClinicalTrialsFeeds.org, U.S. National Institutes of Health Clinical Trials Search Delivered via RSS. Last updated: Nov. 24, 2009, Verified by Instituto Nacional de Ciencias Medicas y Nutricion Salvador Zubiran, No. 2009. 10 pages.

Effect of a multidisciplinary program of weight reduction on endothelial functions in obese women (Abstract). Nocoletti G., Giugliano G., Pontillo A. Cioffi M., D'Andrea F., Giugliano D., Esposito K., Chair of Plastic and Reconstructive Surgery, Second University of Naples, Naples Italy. J. Endocrinol Invest Mar. 2003;26(3) : RC5-88. 1 page.

Obesity and the Risk of Cardiovascular Disease. Mitchell N. Rashid, MD; Francisco Fuetes, MD; Robert C. Tonchon; MD, Paulette S. Wehner MD; Dept. of Internal Medicine, Marshall University School of Medicine, Huntington WV; University of Texas, and the Dept. of Cardiovascular Medicine, Marshall University, Huntington WV. Preventive Cardiology Winter 2003. 6 pages.

Mediastinal Fat, Insulin Resistance, and Hypertension by Arya M. Sharma; Hypertension 2004, 44:117-118: originally published online Jul. 12, 2004 doi: 10.1161/01.HYP.0000137993.7045.82: Copyright 2004 American Heart Assn., ISN: 0194-911X. Online SSSN: 1524-4563. http://hyper.ahajournals.org/content/44/2/117. 3 pages.

The BREAST-Q: Further Validation in Independent Clinical Samples. Stefan J. Cano, Ph.D., Anne F. Klassen, D. Phil., Amie M. Scott, M.P.H., Peter G. Cordeiro, M.D., Andrea L. Pusic, M.D. H.S. S.; Peninsula College of Medicine and Dentistry, McMaster University and Memorial Sloan Kettering Caner Center; Copyright 2012 by the American Society of Plastic Surgeons. DOI: 10.1097/PRS. 0b013e31823 aec6b. 10 pages.

Adipose expression of tumor necrosis factor-alpha: direct role in obesity-linked insulin resistance (Abstract). Hotamisligil GS, Shargill N.S, Spiegelman BM; Dana-Farber Cancer Institute, Boston MA; Science Jan. 1, 1993; 259(509) 87-91. 1 page.

Visceral adipose tissue modulates mammalian longevity. Radhikak Muzumdar[1,2,3], David B. Allison[4], Derek M. Huffman[1,2], Xiaohui MA[1,2], Gil Atzmon[1,2], Francine H. Einstein[1,2], Sigal Fishmant[1,2], Aruna D. Poduvall[1,2,3], Theresa McVei[4], Scott W. Keith[4], and Nir Barzilai[1,2] 1. Inst. For Aging Research, Albert Einstein College of Medicine, Bronx NY, USA 2. Dept. of Medicine, Albert Einstein College of Medicine, Bronx NY, USA 3. Dept. of Pediatrics, Albert Einstein College of Medicine, Bronx NY, USA 4. Section of Statistical Genetics, Univ. of Alabama at Birmingham, Birmingham AL, USA Published in final edited form as: Aging Cell. Jun. 2008; 7(3): 438-440; Correspondence: Nir Barzilai, MD, <barzilai@aecom.yu.edu. 5 pages.

Human mesenteric adipose tissue plays unique role versus subcutaneous and omental fat in obesity related diabetes (Abstract). Yang YK, Chen M, Clements RH, Abrams GA, Aprahamian CJ, Harmon CM; Dept. of Surgery, Univ. of Alabama at Birmingham, USA. Cell Physiol Biochem. 2008; 22(5-6): 531-8. Epub 2008 Dec. 9. 1 page.

Effect of potentially modifiable risk factors associated with myocardial infarction in 52 countries (the INERHEART study): case-control study. Salim Yusuf, Steven Hawken, Stephanie Ounpuu, Tony Dans, Ahlvaro Avezum, Fernando Lanas, Matthew McQueen, Andrzej Budaj, Prem Pais, John Varigos, Liu Lisheng on behalf of the INTERHEART Study Investigators. Lancet 2004; vol. 364: 937-52. Published Online Sep. 3, 2004, Http://Image;thelancet.com/extras/04art8001web.Pdf. 16 pages.

* cited by examiner

ENDOSCOPICALLY-GUIDED TISSUE ASPIRATION SYSTEM FOR SAFELY REMOVING FAT TISSUE FROM A PATIENT

BACKGROUND OF THE INVENTION

1. Field of the Invention

The present invention relates to a novel way of and means for treating abdominal obesity and metabolic syndrome in human patients.

2. Brief Description of the State of Knowledge in the Art

In general, there are three kinds of fat in the human body: subcutaneous fat, intramuscular fat, and visceral fat.

Subcutaneous fat is found underneath the skin, and intramuscular fat is found interspersed in skeletal muscle. Fat in the lower body, e.g. in thighs and buttocks, is subcutaneous. Visceral fat, also known as organ fat or intra-abdominal fat, is located inside the peritoneal cavity, packed in between the internal organs and torso of the abdomen. There are several adipose tissue deposits of visceral fat in the human body, namely: mesenteric, epididymal white adipose tissue, and perirenal deposits. [Adipose tissue as an endocrine organ Kershaw E E, Flier J S. J. Clin. Endocrinol. Metab. 89 (6): 2548-56 (2004).] An excess of visceral fat is known as central obesity, "belly fat," the "pot belly" or "beer belly," where the abdomen protrudes excessively.

Over 250 years ago, Johannes Baptista Morgagni described android obesity as increased intra-abdominal and mediastinal fat accumulation. Back then, he recognized the association between visceral obesity, hypertension, hyperuricemia, atherosclerosis, and obstructive sleep apnea syndrome. [Historical perspective: visceral obesity and its relation to morbidity in Johannes Baptista Morgagni's 'De sedibus et causis morborum per anatomen indagata' Enzi G, Busetto L, Inelmen E M, Coin A, Sergi G Int. J. Obes Relat Metab Disord 27: 534-535 (2003)]

Today, Morgagni's android obesity condition is now described as metabolic syndrome, and is associated with insulin resistance and increased risk of Coronary Heart Disease. The Metabolic syndrome is a condition defined by any three of five risk factors, one of which is waist circumference (female waist>88 cm (>35"), male waist>102 cm.(>40"). The others are triglycerides: (men<40 mg/dl; women<50 mg/dl), HDL cholesterol (>110 mg/dl), blood pressure ($\geqq 130/\geqq 85$ mm Hg), and FBS (>150 ml/dl). [Dyslipidemia of central obesity and insulin resistance. Brunzell, J D, Hokanson, J E Diabetes Care: 22(3); Mediastinal fat, insulin resistance and hypertension. Sharma A M Hypertension: 44:117 (2004)].

Over the past 40 years, the prevalence of obesity in the US increased from 13% to 32%. In 2003-2004, 66% of U.S. adults were overweight or obese.

Abdominal obesity as measured by waist circumference and waist hip ratio (WHR) is an independent predictor of mortality. Marginally increased waist circumference is strongly associated with prevalent hypertension in normal-weight and overweight adults. Also, there is a strong correlation between central (i.e. abdominal) obesity and cardiovascular disease. [Effect of potentially modifiable risk factors associated with myocardial infarction in 52 countries. Yusuf S, Hawken S, Ounpu S, Dans T, Avezum A, Lanas F, McQueen M, Budaj A, Pais P, Varigos J, Lisheng L, Lancet 364: 937-52 (2004).] Because of this, the WHR ratio has been used as a measure of obesity and is an indicator or measure of the health of a person, and the risk of developing serious health conditions. Research shows that people with "apple-shaped" bodies (with more weight around the waist) face more health risks than those with "pear-shaped" bodies who carry more weight around the hips. [Waist-hip ratio should replace Body Mass Index as an indicator of mortality risk in older people. Am. J. Clin. Nutrition (Aug. 12, 2006).]

A WHR of 0.7 for women and 0.9 for men have been shown to correlate strongly with general health and fertility. Women within the 0.7 range have optimal levels of estrogen and are less susceptible to major diseases such as diabetes, cardiovascular disorders and ovarian cancers. Men with WHR's around 0.9, similarly, have been shown to be more healthy and fertile with less prostate cancer and testicular cancer. Studies show that 80 percent of women over the age of 18 have a WHR of at least 0.9. This is a 40 percent increase since 2002, and it keeps increasing.

Although maintaining a healthy weight is a cornerstone in the prevention of chronic diseases and premature death, maintaining a healthy waist size should also be an important goal.

Markedly obese patients are typically directed towards diet and exercise programs, and failing that, presented with the option of bariatric surgery or living with and dying from the increased morbidity of obesity. After bariatric surgery, plastic surgeons perform skin excisions of the redundant folds of tissue remaining on patients who had lost 50-200 lbs. These post-bariatric surgery patients are frequently nutritional cripples with hypoalbuminemia, cirrhosis, and renal stones and suffer increased complications reflecting their impaired nutritional status.

Traditional plastic surgical approaches have been cosmetic, targeted only at removing (i) localized subcutaneous fat deposits in non-obese or modestly obese patients, and (ii) the redundant folds of abdominal wall or pannus that remain after massive weight loss from gastric banding or intestinal bypass procedures.

Before subcutaneous liposuction, combined hemostasis and analgesia is achieved in the patient by infusing tumescent solutions of lactated Ringer's solution, containing dilute amounts of xylocalne and epinephrine. Performing tumescent liposuction in this manner allows increased volumes of fat to be removed and obviates the need for general anaesthesia which, in turn, facilitates outpatient surgery in office-based facilities. [Tumescent Technique Klein, J. Mosby (2000).]

Studies have now shown large volume (subcutaneous) liposuction and abdominoplasty as feasible alternatives for improving body shape. [Large-volume liposuction and extensive abdominoplasty: a feasible alternative for improving body shape. Cardenas-Camarena L, Gonzalez L E Plast Reconstr Surg. 102: 1698-707 (1998).] Clinical studies have shown large volumes of fat can be safely removed in serial liposuction procedures performed at safe intervals. Pilot studies have also shown improvement in the cardiovascular risk profile with large volume subcutaneous liposuction. [Improvements in cardiovascular risk profile with large-volume liposuction: a pilot study. Giese S Y, Bulan E J, Commons G W, Spear S L, Yanovski J A. Plastic Reconstr Surg. 108 510-21 (2001).] However, it should be noted that such large volume subcutaneous liposuction approaches are still mainly cosmetic, as only the less metabolically active, subcutaneous fat is addressed and removed during such procedures.

Recently, animal research has discovered that only the removal of visceral fat in mice has been shown to stop insulin resistance. [Visceral fat removal stops insulin resistance. Barzilai N. Diabetes 51: 2951-2958 (2002).] Increased visceral fat shortens mammalian longevity and its removal lengthens it. [Visceral adipose tissue modulates mammalian longevity. Muzumdar R., Allison D B, Huffman, D M, Xiaohui M, Einstein, F H, Fishman S, Poduval A D, McVei T, Keith, A W, Barzilai, N. Aging Cell 7(3) 438-440 (2008).]
[The effect of fat removal on glucose tolerance is depot specific in male and female mice. Haifei S, Strader A D, Woods, S C, Seeley, R J Am. J. Physiol Endocrinol Metab 293: E1012-1020 (2007).]

Also, in Brazil, clinical trials are being carried out with partial omentectomy to determine the effect on insulin sensitivity. However, such studies have used direct surgical excision, posing high risk of vascular injury, with concomitant bleeding and vascular compromise of the intestine. [Surgical removal of visceral fat tissue (omentectomy) associated to bariatric surgery: effect on insulin sensitivity. Clinical Trials NCT00545805 University of Campinas, Brazil.]

Thus, while there is great promise that the removal of visceral fat in the mesenteric region of human patients stands to ameliorate the metabolic syndrome and abdominal obesity, and reduce morbidity due to obesity, there is a great need in the art for a new and improved method of and apparatus for safely removing visceral fat in human patients, without employing direct surgical excision and posing high risk of vascular injury with concomitant bleeding and vascular compromise of the intestine, associated with conventional surgical procedures and apparatus.

OBJECTS OF THE PRESENT INVENTION

Accordingly, it is a primary object of the present invention to provide a new and improved method of and apparatus for safely removing mesenteric fat in human patients to ameliorate the metabolic syndrome, or abdominal obesity, while avoiding the shortcomings and drawbacks of conventional surgical procedures and apparatus.

Another object of the present invention is to provide such an apparatus in the form of a laparoscopically-guided intra-abdominal liposuction system including a powered hand-supportable instrument held by a surgeon and having an electro-cauterizing cannula assembly for the safe removal of visceral fat from the mesenteric region of a patient, through a small incision in the patient's body.

Another object of the present invention is to provide such a laparoscopically-guided intra-abdominal liposuction system, designed for safely removing visceral fat from the mesenteric region of a patient.

Another object of the present invention is to provide such a laparoscopically-guided intra-abdominal liposuction system, wherein the powered hand-supportable instrument has a bipolar electro-cauterizing cannula assembly, provided with a moving inner cannula, supported in a stationary outer cannula connected to the hand-supportable housing of the instrument.

Another object of the present invention is to provide a novel method of and apparatus for performing laparoscopic mesenteric liposuction for ameliorating the metabolic syndrome, or abdominal obesity of the patient.

Another object of the present invention is to provide such a method comprising the steps of inserting a laparoscopic instrument and an electro-cauterizing liposuction instrument into the mesenteric region of a patient, for the purpose of safely removing visceral fat to ameliorate the metabolic syndrome, or abdominal obesity of the patient.

Another object of the present invention is to provide a novel method of laparoscopically-guided intra-abdominal liposuction, involving the simultaneously infusion of a tumescent solution into the mesenteric region of treatment, while synchronizing that infusion with the forward or return ("action") stroke of the inner cannula of the twin (dual) cannula assembly of the instrument.

A further object of the present invention is to provide a novel system for removing both subcutaneous and visceral fat deposits in a minimally invasive manner.

Yet a further object of the present invention is to provide a novel method of minimally invasive liposuction which is equally applicable to both subcutaneous and visceral fat deposits.

These and other objects of the present invention will be described in greater detail hereinafter in the claims to invention appended hereto.

BRIEF DESCRIPTION OF THE DRAWINGS

The above Objects of the Present Invention will be more fully understood when taken in conjunction with the following FIGure Drawings, wherein like elements are indicated by like reference numbers, wherein:

FIG. 2B1 is a first cross-sectional view of the bipolar twin-cannula assembly shown in FIG. 2B;

FIG. 2B2 is a second cross-sectional view of the twin-cannula assembly shown in FIG. 2B;

FIG. 2B3 is an enlarged cross-sectional view of the distal portion of the twin-cannula assembly shown in FIG. 2B, showing its integrated irrigation channel, and irrigation aperture formed in the outer cannula of the twin-cannula assembly;

DETAILED DESCRIPTION OF THE ILLUSTRATIVE EMBODIMENTS OF THE PRESENT INVENTION

In general, the method of treatment according to the present invention involves performing vacuum-assisted aspiration of mesenteric fat from a patient, using either an "open direct-viewing" based laparotomy procedure, or minimally-invasive, "laparoscopic" based procedure.

The open direct-viewing based procedure involves a surgical team making a direct laparotomy incision into the abdomen of the patient using their own direct human vision to guide their surgical instruments, while performing a visceral liposuction procedure/method in accordance with the principles of the present invention.

The laparoscopic-based procedure involves a surgical team making one or more limited access portals into the patient's abdomen and using laparoscopic and/or camera monitor assistance for their human vision, while performing the visceral liposuction procedure/method in a minimally invasive fashion according to the principles of the present invention.

Using either method, visceral fat is safely removed from the mesenteric region of a patient to help to ameliorate the metabolic syndrome, and/or abdominal obesity.

Figure 1:
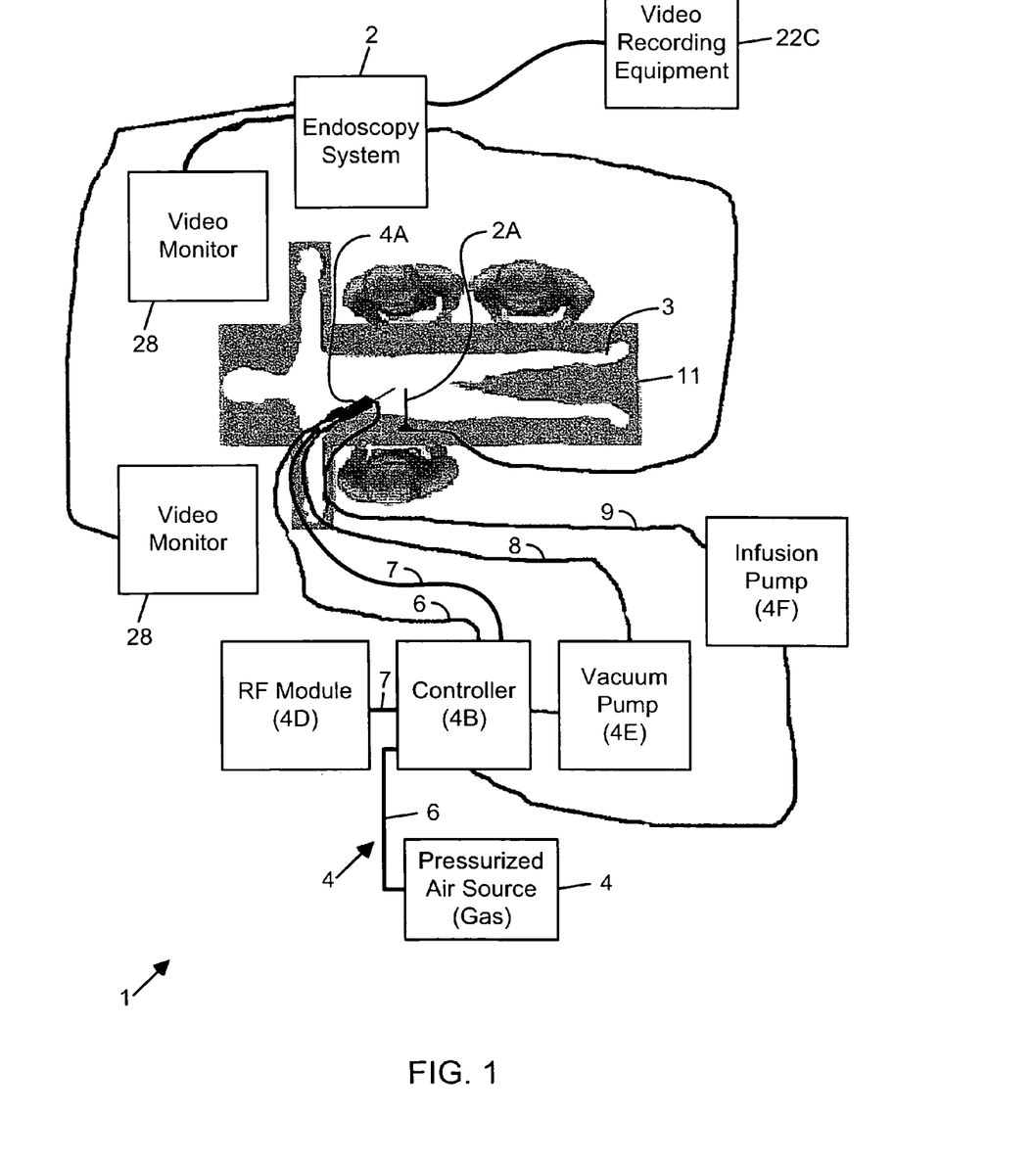
FIG. 1 is a system block diagram of the laparoscopically-guided bipolar power-assisted twin-cannula liposuction system of the present invention, showing an obese patient in an operating room undergoing a mesenteric liposuction procedure carried out using the same.
Figure 4:
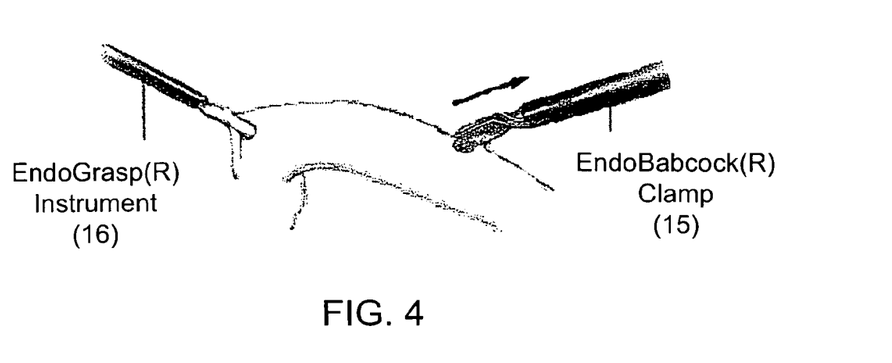
FIG. 4 is a perspective view of the patient's abdominal region during the first phase of a mesenteric liposuction procedure of the present invention, showing the inspection of the small bowel and placing a region of proximal jejunum under tension between two graspers for treatment, following creation of routine laparoscopy portals and customary $CO_2$ infusion for abdominal distension.

In FIGS. 1 and 4, there is shown a preferred apparatus for performing either versions of the mesenteric liposuction method of the present invention, typically in an operating room environment.

As shown in FIGS. 1 and 2, the apparatus of the present invention 1 comprises: an endoscopy (e.g. laparoscopy) system, or laparoscope 2 having (i) video probe 2A for insertion into the patient 3, (ii) one or more video monitors (e.g. LCD displays and controller) 2B for displaying to surgeons and assistants, real-time digital color video images of the patient's abdominal region captured along the field of view (FOV) of the video probe 2A, and (iii) digital recording equipment 2C for recording captured digital video during the operation and marking the same by the surgeons, as required; a bipolar electro-cauterizing twin-cannula powered liposuction system 4 having (i) an air-powered hand-supportable instrument 4A provided with a self-irrigating bipolar electro-cauterizing twin-cannula assembly 5, (ii) a system controller 4B connected to the hand-supportable instrument 4A by way of a flexible multi-lumen cable assembly 4C, for supplying (i) pressurized air streams 6 to drive the inner cannula of the hand-supportable instrument 4A, and (ii) RF-power signals 7 generated by an RF signal generating module 4D for powering the self-irrigating bipolar electro-cauterizing twin cannula assembly 5, as taught in U.S. Pat. No. 7,384,417 B2; a vacuum line 4E connected to the base portion of the inner cannula via a flexible tubing, for aspirating visceral fat through the aspiration aperture 9 of the twin cannula assembly 5 during system operation; and an infusion pump 4F controlled by the system controller 4B, for periodically or continuously infusing solution near the distal portion of the cannula assembly 5 during system operation; an operating table 11 for supporting a patient; and other operating room equipment including high intensity lighting apparatus, retraction clips, stitches etc.

Figure 2A:
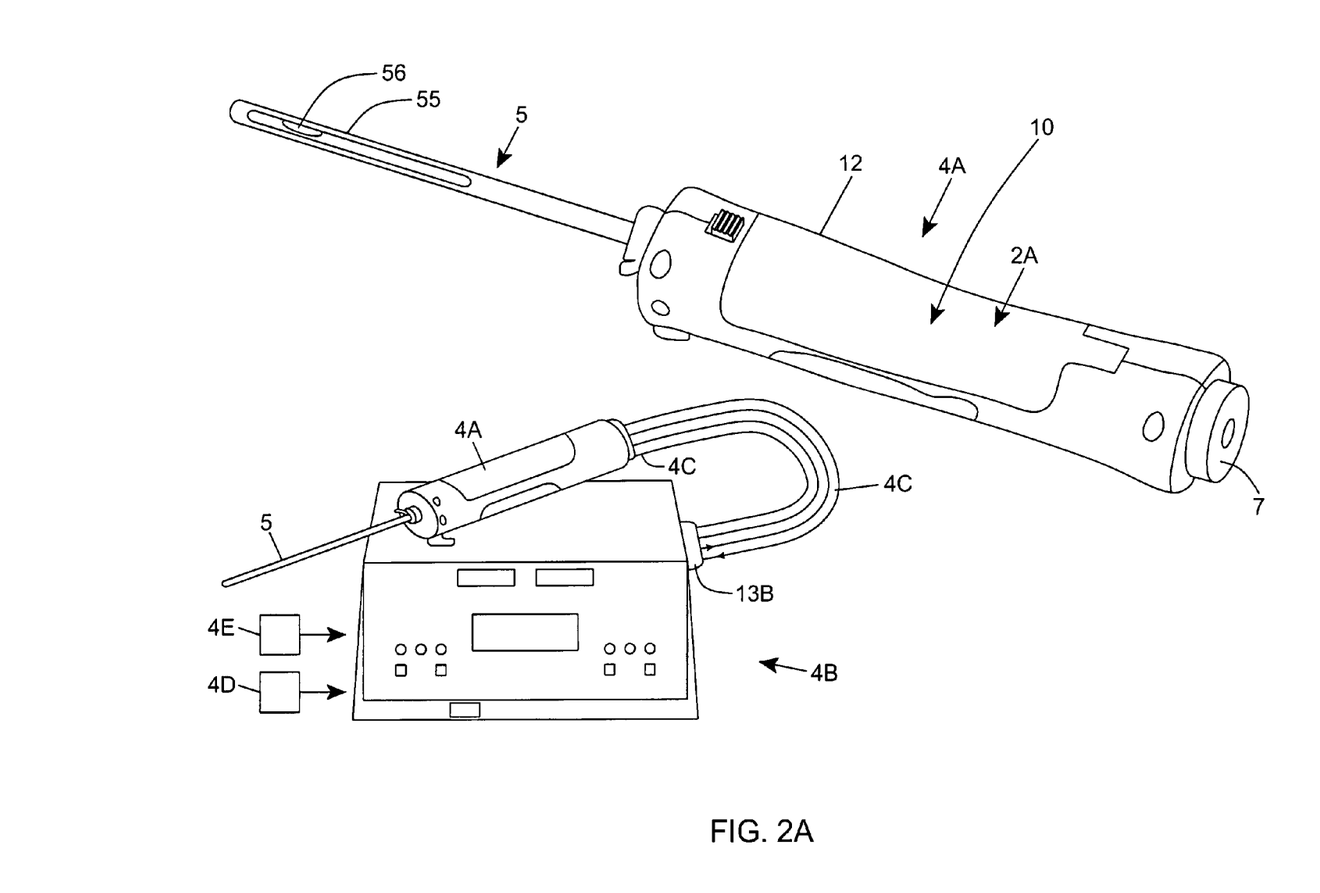
FIG. 2A is a perspective view of the bipolar electro-cauterizing irrigating twin-cannula liposuction instrumentation system of the present invention, shown in the system of FIG. 1, wherein an inner cannula is mechanically reciprocated within a stationary outer cannula of the hand-supportable instrument, while the inner cannula is operably affixed to a vacuum source and the hand piece is attached to a quick connect cable assembly that connects it to the (digital signal processor) DSP controller, providing a closed feedback loop for safe control of reciprocation rate and stroke, control of bipolar electro-cautery, and synchronized pulsed tumescent infusion during system operation.

In FIG. 2A, the hand-supportable electro-cautery liposuction instrument 4A of FIG. 1 is shown in greater detail. As shown, the instrument has a hand-supportable housing 12 into which the self-irrigating bipolar electro-cauterizing cannula assembly 5 is removably inserted by the surgeon. In the illustrative embodiment, the housing has a side panel which opens 12A for servicing. The rear portion of the housing has a connector 13A into which one end of the flexible cable assembly 4C snap-fits as taught in U.S. Pat. No. 7,384,417 B2. Within the housing, a motor 10 (i.e. inner cannula driving mechanism) is provided for reciprocating the inner cannula within the outer cannula during instrument operation. The "motor" 10, as defined herein and in the Claims to Invention, can be realized using any or more available motion-drive technologies such as, for example: a pressurized-air cylinder driven by source of pressurized gas (e.g. $CO_2$); an electro-magnetic motor driven by electrical current delivered at a given voltage; or other powered-type device capable of reciprocating the inner cannula within the outer cannula assembly.

Figure 2B:
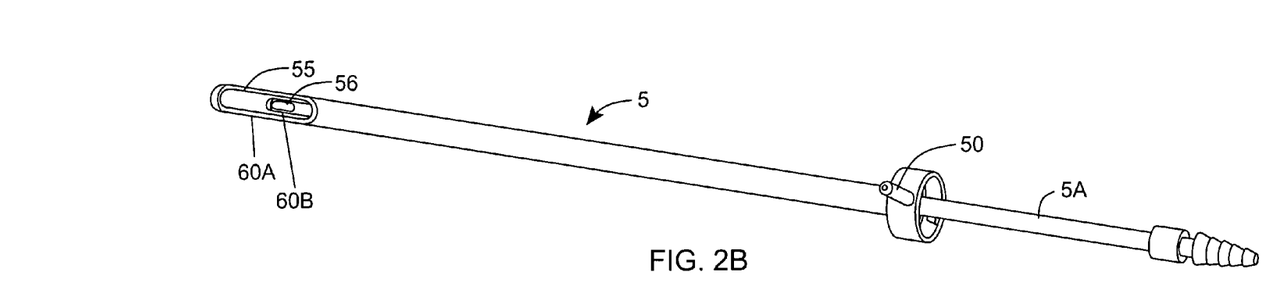
FIG. 2B is a perspective view of a bipolar electro-cauterizing twin-cannula assembly shown in FIG. 2, having bipolar electro-cauterizing electrodes formed about the aspiration aperture of the twin cannula assembly, and an integrated irrigation channel (lumen) formed in the outer wall portion of its outer cannula, and irrigation aperture formed at the distal tip portion thereof, for expressing irrigation fluid supplied to the irrigation channel from an irrigation fluid supply system.
Figure 2B:
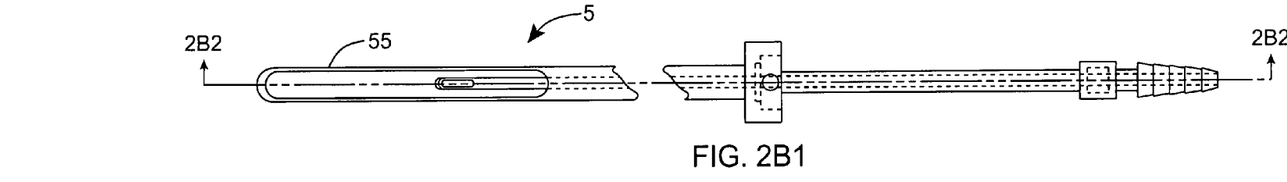
Figure 2B:
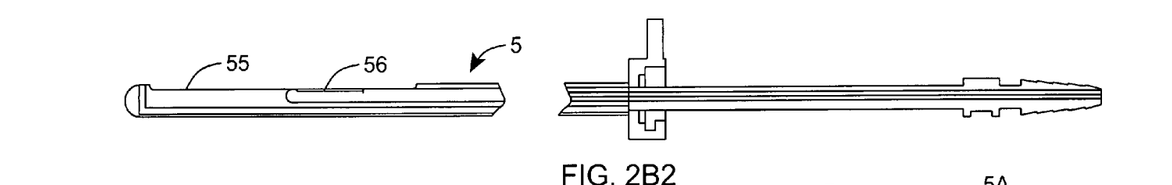

As shown in FIGS. 2B, 2B1 and 2B2, the bipolar electro-cauterizing cannula assembly 5 has a distal portion and an proximate portion, and includes an outer cannula 5A having a base portion that inserts within said hand-supportable housing and has an elongated aperture 56 formed at the distal portion of the outer, cannula. The cannula assembly 5 also includes an inner cannula 5B supported within the outer cannula 5A, and having an aspiration aperture 55, and a base portion which is operably connected to vacuum pump 4E, by way of a flexible tubing 8, for aspirating visceral fat tissue from the mesentery of the patient. As shown in FIG. 2B, electrically-conductive electrodes 60A and 60B are formed along the elongated aperture 56 and aspiration aperture 55 of the outer and inner cannulas, respectively. The purpose of electrodes 60A and 60B is to electro-cauterize visceral fat tissue as the fat tissue is being aspiration through the aspiration aperture, with or without irrigation.

Figure 2B:
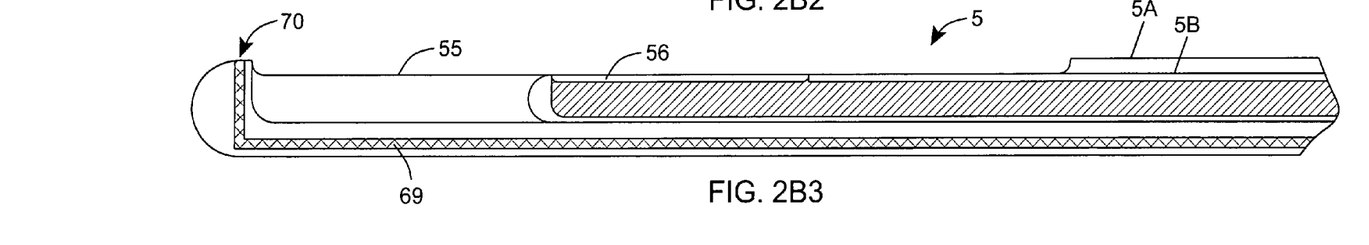

As shown in the illustrative embodiment of FIG. 2B3, a fluid or irrigation channel 69 is formed in the outer cannula 5A and terminates at the distal portion of the outer cannula lumen. However, in other embodiments of the present invention, the irrigation channel 69 can be formed externally to the outer cannula 5A, and terminate at the distal portion thereof, to deliver irrigation fluid in the region where the aspiration aperture 56 reciprocates during instrument operation. As shown in FIG. 2B, the base portion of the outer cannula 5A has a small irrigation connector 50 for receiving the open end portion of a length of flexible tubing 9 supplying the irrigation fluid to the outer cannula 5A, as part of the infusion pump system 4F.

During system operation, the infusion pump 4F delivers controlled amounts of fluid to the irrigation channel 69, over short periods of time, in synchronization with either the forward or return stroke of the inner cannula 5B within the outer cannula 5A, so that fluid flows out of the irrigation aperture 70 and proximate to the elongated aperture 56, while visceral fat is being electro-cauterized by electrodes 60A and 60B and aspirated through the reciprocating aspiration aperture 55 of the hand-supportable liposuction instrument 5.

Figure 2C:
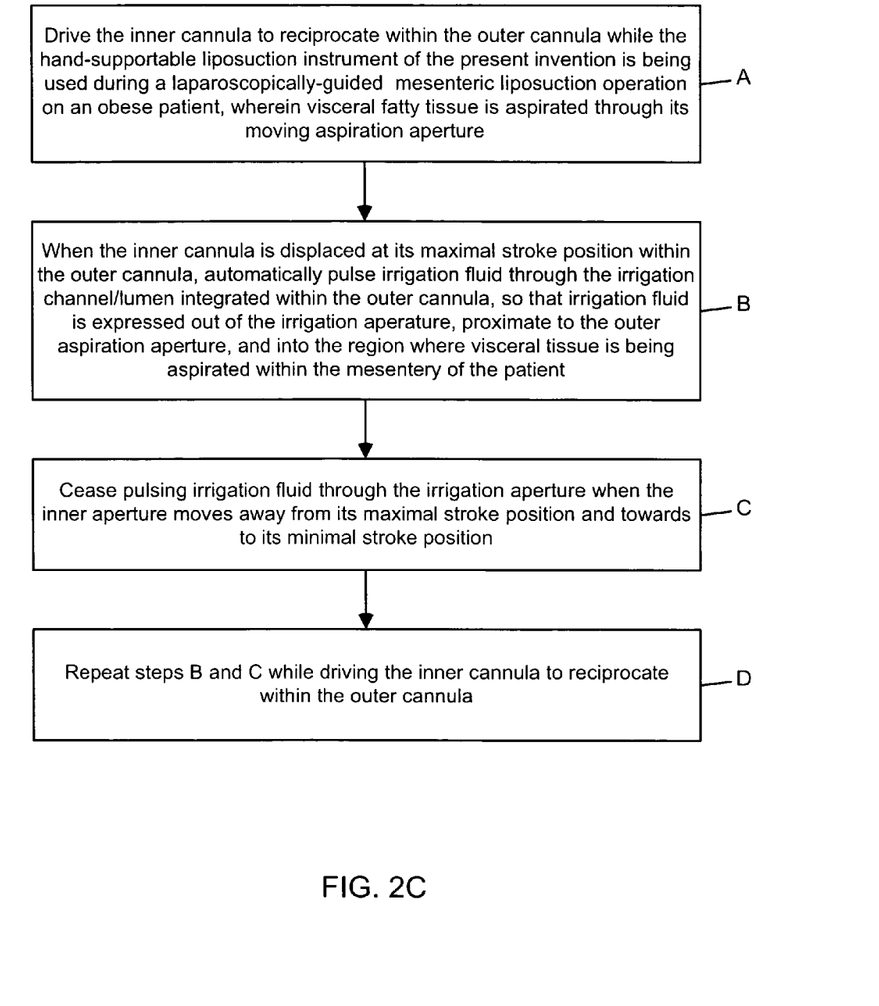
FIG. 2C is a flow chart describing the operation of the infusion pump of FIG. 1 in cooperation with irrigating electro-cauterizing visceral liposuction instrument illustrated in FIGS. 2A through 2B3.

FIG. 2C describes the primary control operations performed by system controller 4B during fluid irrigation delivery operations using the surgical system of FIG. 1. Specifically, as indicated at Step A in FIG. 2C, the inner cannula is driven to reciprocate within the outer cannula while the hand-supportable liposuction instrument is being used during a laparoscopically-guided mesenteric liposuction operation on an obese patient, wherein visceral fatty tissue is aspirated through its moving aspiration aperture. As indicated at Step B, when the inner cannula is displaced at its maximal stroke position within the outer cannula, irrigation fluid is automatically pulsed through the irrigation channel/lumen integrated within the outer cannula, so that irrigation fluid is expressed out of the irrigation aperture, proximate to the outer aspiration aperture, and into the region where visceral tissue is being aspirated within the mesentery of the patient. As indicated at Step C, the automatic pulsing of irrigation fluid through the irrigation aperture is ceased when the inner aperture moves away from its maximal stroke position and towards its minimal stroke position. As indicated at Step D, the operations of Steps B and C are repeated while driving the inner cannula to reciprocate within the outer cannula. The control routine of FIG. 2C will be realized using computer programming techniques well known in the art.

As shown in FIG. 2F, the laparoscopic instrumentation 2 will typically further include a laparoscope with a viewing portal and camera 2A, trochars for penetrating the abdomen, laparoscopic graspers, laparoscopic scissors, a laparoscopic bipolar cautery device, a $CO_2$ infusion tube, as described in detail in U.S. Pat. No. 7,384,417 B2, incorporated herein by reference.

As shown in FIG. 2G, the infusion pump 4F will typically include a roller pump which compresses the tubing to create forward flow, as disclosed in U.S. Pat. No. 7,384,417 B2 incorporated herein by reference. More ideally the infusion pump 4F will be designed for a pulsatile flow of irrigation fluid through cannula 20 so that controlled amounts of fluid are delivered under short periods of time to facilitate synchronization with either the forward or return stroke of the inner cannula 5B.

Having described the preferred apparatus of the present invention, it is appropriate at this juncture to describe the preferred method of treating patients according to the present invention, with reference to the method flow chart set forth in FIG. 3.

Figure 3A:
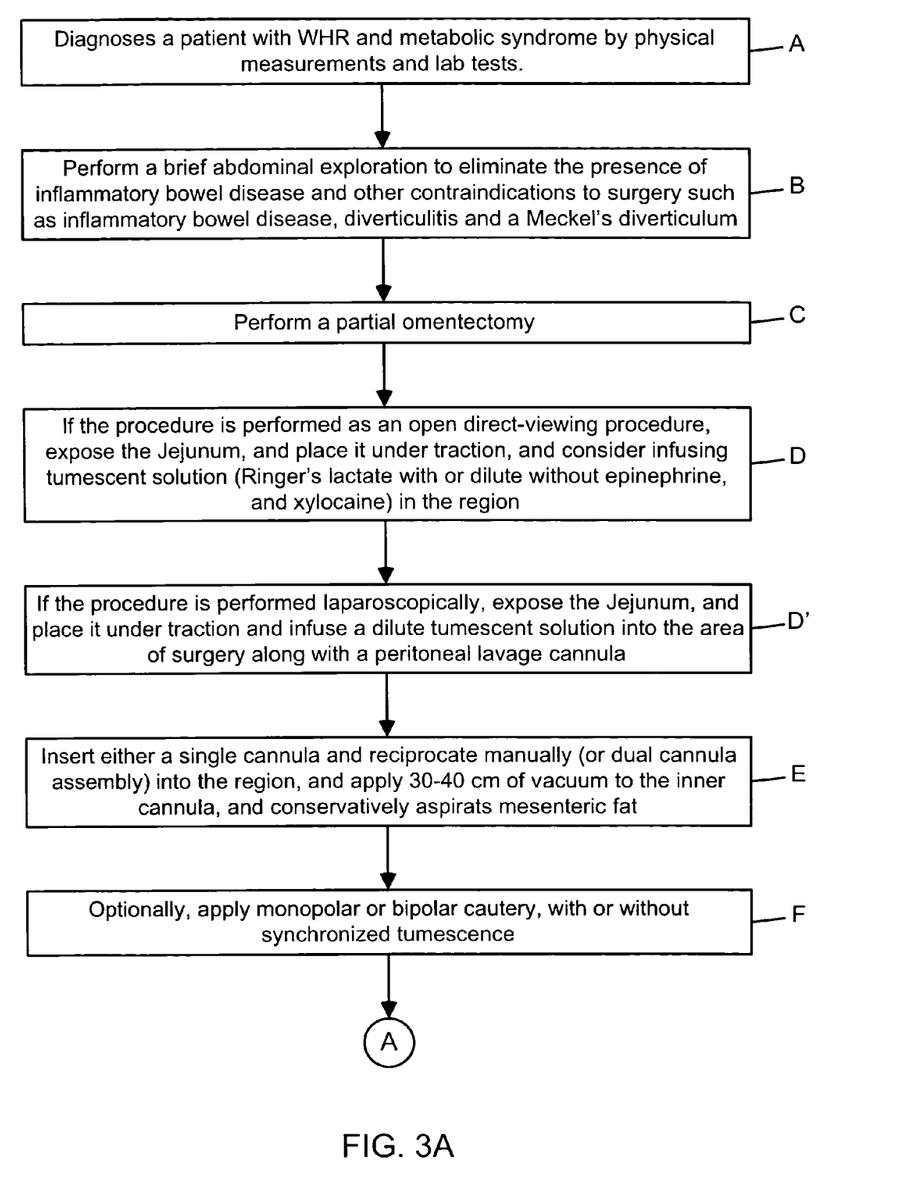
FIGS. 3A and 3B is a flow chart illustrating the primary steps carried out during the illustrative embodiment of the method of mesenteric liposuction according to the present invention, comprising diagnosis, exploration, partial omentectomy, small bowel mesenteric liposuction, large bowel mesenteric liposuction, followed by subcutaneous liposuction, abdominal and dermatolipectomies as indicated.

As indicated in Step A in FIG. 3A, the surgeon diagnoses a patient with metabolic syndrome and/or obesity, using the waist-to-hip ratio (WHR), by physical measurements and lab tests.

As indicated in Step B in FIG. 3A, the surgeon performs a brief abdominal exploration or inspection to eliminate the presence of inflammatory bowel disease and other contraindications to surgery, such as, diverticulitis and a Meckel's diverticulum, or any other pathology. At her option, the surgeon may infuse a tumescent solution (Ringer's lactate with or without dilute epinephrine, and with or without xylocalne) as described above to prepare the area for treatment.

As indicated in Step C in FIG. 3A, the surgeon performs a partial omentectomy by removing the redundant omental apron.

As indicated in Step D in FIG. 3A, when performed as an open direct-viewing procedure, the omentum is retracted and the jejunum is exposed. Either by the hands of an assistant in an open procedure or with aid of atraumatic laparoscopic graspers [Endo Babcock or Dolphin Nose Grasper], the proximal jejunum is isolated and placed under gentle tension. One atraumatic grasper is inserted in the right upper quadrant for retraction of the jejunum towards the liver, and a second atraumatic grasper is inserted in the left lower quadrant, placed on a section of jejunum approximately 6 to 8 inches distal to the previously placed grasper, and retracted caudally towards the left lower quadrant. The jejunum is placed under tension and the mesentery exposed and straightened.

As indicated at Step D in FIG. 3A, when performed as a laparoscopic procedure, a pneumoperitoneum is created in the usual fashion and the trochars are inserted so the procedure may be performed under laparoscopic guidance with multiple monitors. A partial omentectomy may be carried out by removing the caudal portions of the omentum. When performed laparoscopically, omentum is removed in strips to facilitate removal through laparoscopic portals. Care is taken to obtain strict hemostasis and to preserve an apron of protective omentum while it is substantially shortened and defatted.

FIG. 4 depicts the bowel grasped between two clamps to tent up the mesentery.

Figure 5:
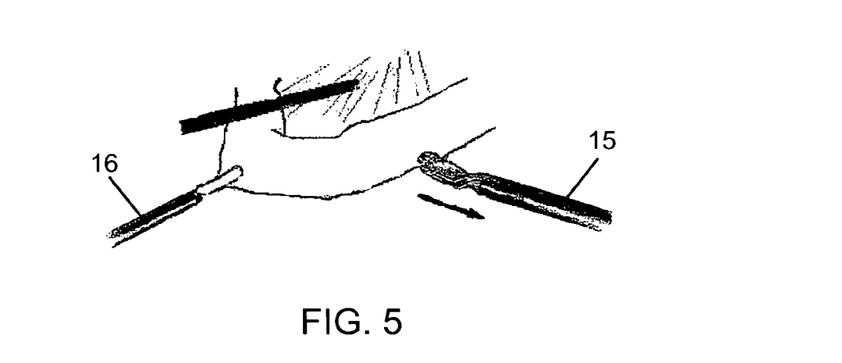
FIG. 5 is perspective view of the patient's abdominal region during a second phase of the mesenteric liposuction procedure of the present invention, showing the insertion of a cannula into the mesentery for infusion of tumescent solution.

FIG. 5 depicts a cannula inserted into the tented mesentery to infuse tumescent solution.

Figure 6:
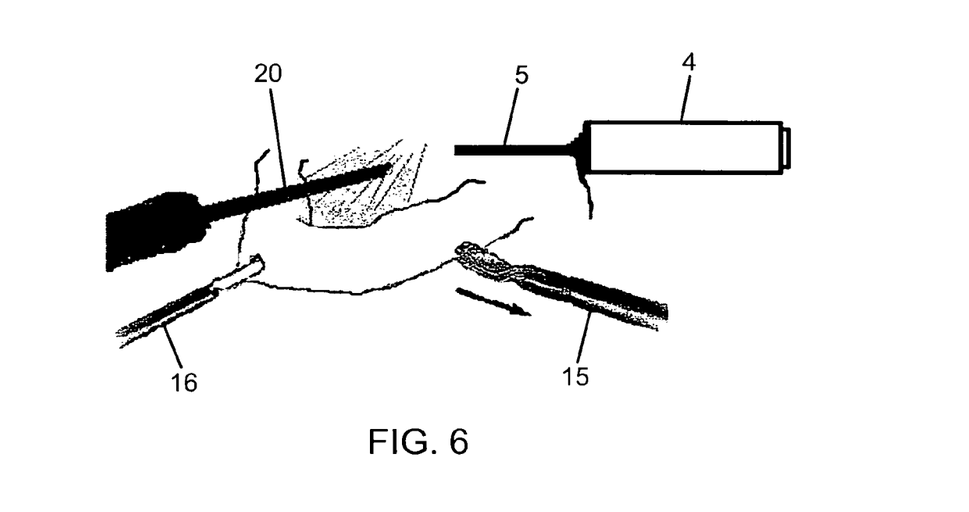
FIG. 6 is perspective view of the patient's abdominal region during a third phase of the mesenteric liposuction procedure of the present invention, showing the insertion of the bipolar electro-cauterizing twin-cannula liposuction instrument shown in FIG. 1, into the mesentery of the patient and fat removal by way of liposuction under laparoscopy guidance with the laparoscope shown.
Figure 7:
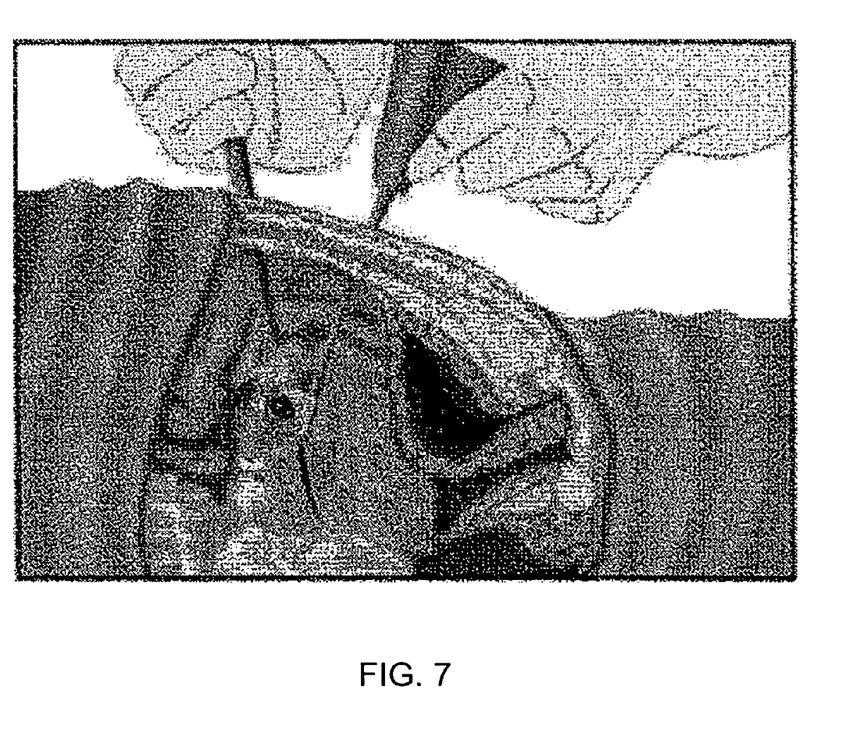
FIG. 7 is a cross-section partially cut away view of the patient's abdominal region during a later phase of the mesenteric liposuction procedure of the present invention, showing the aspiration and electro-cauterization of visceral fatty tissue in the mesentery, using the laparoscopically-guided irrigating bipolar electro-cauterizing twin-cannula liposuction instrumentation of the present invention.

As indicated in Step E in FIG. 3A, a retractor is inserted through the right lower quadrant and placed posteriorly beneath the tented mesentery. An incision is made anteriorly in the mesentery, approximately /2;3 of the distance between its base and the bowel. The surgeon then inserts either a single cannula through the right lower quadrant and into an anterior incision in the jejunal mesentery, and reciprocates it manually, or preferably inserts the power-assisted twin cannula assembly 5 into the region, and applies 30-40 cm Hg of vacuum to the inner cannula, and conservatively aspirates mesenteric fat. FIG. 6 depicts insertion of the twin cannula device 5 into the previously tumesced and tented mesentery.

When using a laparoscopically-guided electro-cauterizing twin-cannula liposuction instrument system shown in FIGS. 1 and 2, there is much less risk of vascular disruption or visceral injury than when using single cannula instrument, because the twin cannula instrument protects the adventitia of the arboreal blood vessels from injury, and allows treatment of larger areas more rapidly and effectively.

As indicated in Step F in FIG. 3A, the surgeon optionally, applies monopolar or bipolar cautery, with or without synchronized tumescence. By including a separate fluidic channel in the outer cannula, extending from its base to its tip, it is possible to synchronize a pulsed infusion of tumescent solutions or irrigation (e.g. lactated Ringer's solution with or without small amounts of epinephrine (e.g. 1:100,000-1:400,000) through this additional channel in the tip of the twin cannula assembly with the advancement of the inner cannula, to facilitate fat aspiration with a sump effect. Alternatively, a totally separate cannula may be placed with the mesentery and used for pulsatile or non-pulsatile, synchronized or unsynchronized infusion near the tip of the twin cannula assembly 5.

By eliminating the battering ram effect of a reciprocating cannula and the need for tumescent solution for hemostasis, twin cannula liposuction allows the minimally invasive removal of soft tissue in any location, including the intestinal mesentery by either open or laparoscopic approaches. Unlike single cannula liposuction cannulas, the tube-within-a-tube construction of the twin cannula assembly, taught in U.S. Pat. No. 7,384,417 B2 is particularly suited to a laparoscopic approach as all viscera are spared disruption from the moving member except the limited area of fat being aspirated in the mesentery adjacent to the outer cannula slot. The relatively stationary outer cannula reduces friction caused by the continually reciprocating inner cannula and the laparoscopy portal. Placement of the outer cannula 5A is positional, rather than actively reciprocating, to avulse particles of fat.

Twin cannula mesenteric liposuction (TCML) according to the principles of the present invention described above, thus allows direct correction of abdominal obesity, and in a less invasive and dramatically immediate fashion without the untoward nutritional consequences, hepatic, or renal complications of gastric bypass or banding procedures.

The use of twin cannula liposuction, with or without bipolar cautery hemostasis and with or without a synchronized pulsed infusion of tumescent or irrigation solution through the cannula, offers a controlled, rapid, and safer way of treating a length of intestine with much less risk of bleeding or vascular injury.

Although bipolar hemostasis obviates the need for tumescence with epinephrine containing solutions, small amounts of epinephrine could be added to small pulses of lactated Ringer's solution, with or without small quantities of local anaesthetic, which are synchronized with the advancement of the inner cannula within the outer cannula.

Since the irrigation solution is immediately aspirated through the aspiration aperture 55 of the twin (twin) cannula assembly 5 of FIG. 2A, the systemic effects of vasopressor and local anesthetics during twin cannula synchronized tumescence (TCST) would be more limited than an alternative means, such as infusion of a similarly dilute epinephrine and xylocalne in lactated Ringer's solution with a Tenckoff catheter via peritoneal lavage.

Epidural or general anaesthesia could replace or augment synchronized infusion or peritoneal lavage. Although TCST is the preferred embodiment of the described method, the present invention contemplates choosing modalities that are optimized for each individual patient's physiologic and cardiovascular status, and concentrations of xylocalne and epinephrine in the employed solutions from zero to therapeutic, as the situation dictates.

Figure 3B:
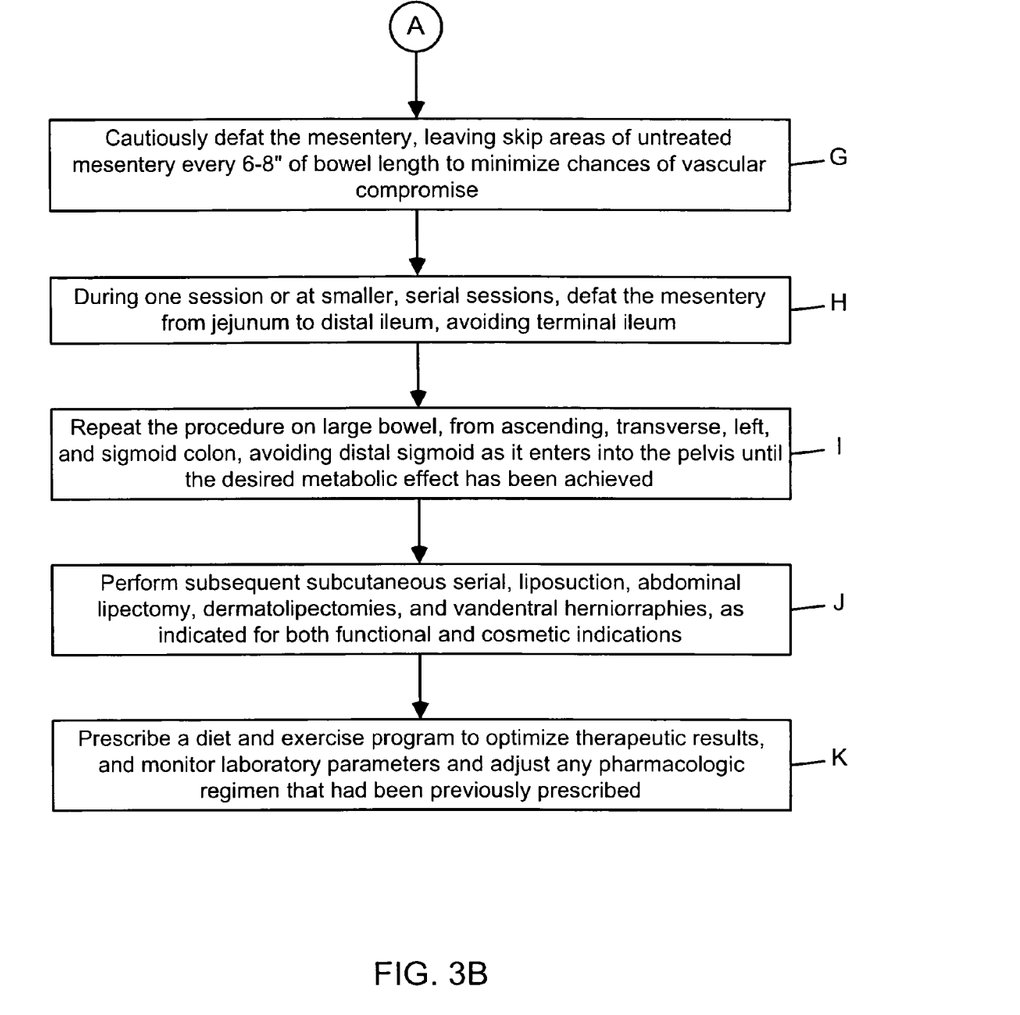

As indicated in Step G in FIG. 3B, the surgeon cautiously defats the mesentery, leaving skip areas of untreated mesentery every 6-8" of bowel length to minimize chances of vascular compromise. This step can be achieved by applying a vacuum of 30-40 cm Hg, and defatting the mesentery by reciprocating a single cannula manually, or in the preferred embodiment, initiating mechanical reciprocation of the inner cannula 5B within the outer cannula 5A of the transiently stationary twin cannula assembly 5. Care is taken to retain some fat and avoid creating defects that might allow intestine to herniate through, and any perforations in the mesentery are closed to eliminate this hazard. The area of treatment is inspected for hemostasis and any defects in the mesentery repaired. The jejunum between clamps is inspected for good vascular supply.

As indicated in Step H IN FIG. 3B, during a single session or during smaller, serial sessions, the surgeon defats the mesentery from jejunum to distal ileum, avoiding terminal ileum. Then, as with the open approach, a small area is skipped much like a radiating spokes on a wheel to assure continuity of blood supply, and the next 8" area of jejunum is tented and the procedure repeated until the terminal ileum is reached and left untreated. Any difficulties with hemostasis or questionable vascular viability of the bowel indicate the necessity of a resection and possible conversion to an open procedure.

As indicated in Step I in FIG. 3B, the surgeon repeats the procedure on the large bowel and/or the small bowel for greatest effect. The mesentery of the large bowel would be approached from the ascending colon to the sigmoid colon, avoiding the area surrounding the ileocecal valve, and the distal sigmoid colon as it descends into the pelvis, and the mesentery to any areas of large bowel which appear grossly involved with diverticulitis.

As indicated in Step J in FIG. 3B, the surgeon performs subsequent subcutaneous serial, liposuction, abdominal lipectomy, dermatolipectomies, and ventral herniorraphies, as indicated for both functional and cosmetic indications. Large volume subcutaneous liposuction, panniculectomy, abdominoplasty, repair of any ventral hernias or diastasis recti could be carried out in serial sessions to obtain a much tightened abdominal corset for both functional and cosmetic improvement. The majority of these procedures can be performed under conscious sedation and on an ambulatory basis on these patients with minimal complications because of their improved metabolic profiles.

As indicated in Step K in FIG. 3B, the surgeon prescribes a diet and exercise program to optimize therapeutic results, and monitors laboratory parameters and adjust any pharmacologic regimen that had been previously prescribed.

Several modifications to the illustrative embodiments have been described above. It is understood, however, that various other modifications to the illustrative embodiment of the present invention will readily occur to persons with ordinary skill in the art. All such modifications and variations are deemed to be within the scope and spirit of the present invention as defined by the accompanying Claims to Invention.

What is claimed is:

1. An endoscopically-guided electro-cauterizing power-assisted tissue aspiration system, for safely removing visceral fat tissue from a patient having an abdomen including a mesenteric region, said endoscopically-guided electro-cauterizing power-assisted tissue aspiration system comprising:
    an endoscopy system having
        a video probe having a field of view (FOV), for insertion into the patient by one or more surgeons;
        one or more video monitors for displaying, to said one or more surgeons and assistants, digital video images of the patient's abdomen, captured along the FOV of said video probe; and
        digital recording equipment for recording captured digital video images;
    an electro-cauterizing tissue aspiration system including
        (i) a powered hand-supportable instrument including a hand-supportable housing and being provided with an electro-cauterizing cannula assembly having an inner cannula mounted for reciprocating movement within an outer cannula, wherein said inner cannula has an inner aspiration aperture, and wherein said outer cannula is mounted stationary to said hand- supportable housing and has an outer aspiration aperture; and
        (ii) a system controller operably connected to said powered hand-supportable instrument, for supplying power to drive said inner cannula to reciprocate within said outer cannula, and
        (iii) a RF signal generating module for generating RF-power signals functioning as electro-cauterizing signals provided about said outer aspiration aperture of said outer cannula;
    a vacuum pump operably connected to said inner cannula, for aspirating visceral fat tissue from the mesenteric region of said patient, through said outer and inner aspiration apertures of said electro-cauterizing cannula assembly; and an infusion pump controlled by said system controller, for periodically or continuously infusing solution near the distal portion of said electro-cauterizing cannula assembly during aspiration of visceral fat tissue from said patient.

2. An endoscopically-guided power-assisted tissue aspiration system, for safely removing fat tissue from the mesenteric region of a patient having an abdomen including a mesenteric region, said endoscopically-guided power-assisted tissue aspiration system comprising:

an endoscopy system having
a video probe having a field of view (FOV), for insertion into the patient by one or more surgeons, and capturing digital images within said FOV; and
one or more video monitors for displaying, to said one or more surgeons and assistants, digital video images of the patient's abdomen, captured along the FOV of said video probe; and
a power-assisted tissue aspiration system including
a powered hand-supportable instrument including a hand-supportable housing and being provided with a twin-cannula assembly including an inner cannula mounted for reciprocating movement within an outer cannula,
wherein said inner cannula has an inner aspiration aperture, and
wherein said outer cannula is mounted stationary to said hand-supportable housing and has an outer aspiration aperture;
a source of power operably connected to said powered hand-supportable instrument, for supplying power to drive said inner cannula to reciprocate said inner cannula within said outer cannula during tissue aspiration operations; and
a vacuum pump operably connected to said inner cannula, for aspirating visceral fat tissue from the mesenteric region of said patient, through said outer and inner aspiration apertures of said twin-cannula assembly and towards said vacuum pump, while said video probe is capturing digital images of fat tissue within said FOV being removed from said mesenteric region of the patient, and said one or more video monitors are displaying said digital images of said fat tissue.

3. The endoscopically-guided power-assisted tissue aspiration system of claim 2, wherein said powered hand-supportable instrument comprises a RF signal generating module for generating RF-power signals functioning as electro-cauterizing signals provided about said outer aspiration aperture of said outer cannula.

4. The endoscopically-guided power-assisted tissue aspiration system of claim 2, which further comprises an infusion pump controlled by a system controller, for periodically or continuously infusing solution near the distal portion of said twin-cannula assembly during aspiration of fat tissue from said patient.

5. The endoscopically-guided power-assisted tissue aspiration system of claim 3, wherein said source of power comprises at least one of a source of pressurized air, and a source of electrical power.

6. The endoscopically-guided power-assisted tissue aspiration system of claim 3, wherein said endoscopy system further comprises digital recording equipment for recording captured digital video images of said abdominal region, within the FOV of said video probe.

7. A method of safely removing fat tissue from the mesenteric region of a patient's abdomen using an endoscopically-guided power-assisted tissue aspiration system, said method comprising the steps of:

(a) preparing a patient for endoscopically-guided removal of fat tissue from the mesenteric region the patient, using an endoscopy system and a power-assisted tissue aspiration system, wherein said endoscopy system includes
a video probe having a field of view (FOV), for insertion into the patient by one or more surgeons, and capturing digital images of the patient's abdomen within said FOV; and
one or more video monitors for displaying, to said one or more surgeons and assistants, digital video images of the patient's abdomen, captured along the FOV of said video probe; and
wherein said power-assisted tissue aspiration system includes
a powered hand-supportable instrument including a hand-supportable housing and being provided with a twin-cannula assembly including an inner cannula mounted for reciprocating movement within an outer cannula,
wherein said inner cannula has an inner aspiration aperture, and
wherein, said outer cannula is mounted stationary to said band-supportable housing and has an outer aspiration aperture;
a source of power operably connected to said powered hand-supportable instrument, for supplying power to drive said inner cannula to reciprocate said inner cannula within said outer cannula during tissue aspiration operations; and
a vacuum pump operably connected to said inner cannula, for aspirating visceral fat tissue from the mesenteric region of said patient, through said outer and inner aspiration apertures of said twin-cannula assembly and towards said vacuum pump;

(b) inserting said video probe into the abdomen of said patient, and displaying digital video images of the patient's abdomen, captured along the FOV of said video probe;

(c) inserting said twin-cannula assembly into the abdomen of said patient, while digital video images of the patient's abdomen are captured along the FOV of said video probe and displayed on said one or more video monitors;

(d) using said source of power to supply to power and drive said inner cannula to reciprocate said inner cannula within said outer cannula during tissue aspiration operations; and (e) using said vacuum pump to aspirate visceral fin tissue from the mesenteric region of said patient, through said outer and inner aspiration apertures of said twin-cannula assembly and towards said vacuum pump, while said video probe is capturing digital images of fat tissue within said FOV being removed from said mesenteric region of the patient, and said one or more video monitors are displaying said digital images of said fat tissue.

8. The method of claim 7, wherein during step (a) said powered hand-supportable instrument comprises a RF signal generating module for generating RF-power signals functioning as electro-cauterizing signals provided about said outer aspiration aperture of said outer cannula; and wherein during step (e) said RF generating module generates said RF-power signals which are provided about said outer aspiration aperture of said outer cannula during visceral tissue aspiration operations.

9. The method of claim 7, wherein during step (a), said endoscopically-guided power-assisted tissue aspiration system further comprises an infusion pump controlled by a system controller, for periodically or continuously infusing solution near the distal portion of said twin-cannula assembly during aspiration of fat tissue from said patient; and wherein during step (e), said infusion pump periodically or continuously infuses solution near the distal portion of said twin-cannula assembly during aspiration of fat tissue from said patient.

10. The method of claim 7, wherein said source of power comprises at least one of a source of pressurized air, and a source of electrical power.

11. The method of claim 7, wherein during step (a), said endoscopy system further comprises digital recording equipment for recording captured digital video images of said abdominal region; and wherein during step (e), said digital recording equipment records said digital video images of said abdominal region within the FOV of said video probe during visceral tissue aspiration operations.

* * * * *